(12) United States Patent
Cao et al.

(10) Patent No.: US 7,901,882 B2
(45) Date of Patent: Mar. 8, 2011

(54) ANALYSIS OF METHYLATION USING NUCLEIC ACID ARRAYS

(75) Inventors: Yanxiang Cao, Mountain View, CA (US); Shivani Nautiyal, Portola Valley, CA (US); Charles G. Miyada, San Jose, CA (US); Christopher Davies, Walnut Creek, CA (US); Gangwu Mei, Fremont, CA (US); Alan J. Williams, Albany, CA (US); Eric B. Schell, Mountain View, CA (US); John E. Blume, Sunnyvale, CA (US)

(73) Assignee: Affymetrix, Inc., Santa Clara, CA (US)

(*) Notice: Subject to any disclaimer, the term of this patent is extended or adjusted under 35 U.S.C. 154(b) by 14 days.

(21) Appl. No.: 11/695,599

(22) Filed: Apr. 2, 2007

(65) Prior Publication Data
US 2007/0243546 A1 Oct. 18, 2007

Related U.S. Application Data

(60) Provisional application No. 60/788,520, filed on Mar. 31, 2006.

(51) Int. Cl.
C12Q 1/68 (2006.01)
C07H 21/02 (2006.01)
C07H 21/04 (2006.01)

(52) U.S. Cl. ............................ 435/6; 536/23.1; 536/24.3
(58) Field of Classification Search ..... 435/6; 536/23.1, 536/24.3
See application file for complete search history.

(56) References Cited

U.S. PATENT DOCUMENTS

| | | | |
|---|---|---|---|
| 5,118,604 A | 6/1992 | Weissman et al. | |
| 5,217,889 A | 6/1993 | Roninson et al. | |
| 5,474,796 A * | 12/1995 | Brennan | 427/2.13 |
| 5,576,204 A | 11/1996 | Blanco | |
| 5,580,730 A | 12/1996 | Okamoto | |
| 5,710,000 A | 1/1998 | Sapolsky et al. | |
| 5,786,146 A | 7/1998 | Herman et al. | |
| 5,871,917 A | 2/1999 | Duffy | |
| 5,912,147 A | 6/1999 | Stoler et al. | |
| 5,942,609 A | 8/1999 | Hunkapiller et al. | |
| 6,017,701 A | 1/2000 | Sorge et al. | |
| 6,017,704 A | 1/2000 | Herman et al. | |
| 6,156,501 A | 12/2000 | McGall et al. | |
| 6,200,756 B1 | 3/2001 | Herman et al. | |
| 6,214,556 B1 | 4/2001 | Olek et al. | |
| 6,251,594 B1 | 6/2001 | Gonzalgo et al. | |
| 6,265,171 B1 | 7/2001 | Herman et al. | |
| 6,300,071 B1 | 10/2001 | Vuylsteke et al. | |
| 6,309,823 B1 | 10/2001 | Cronin et al. | |
| 6,331,393 B1 | 12/2001 | Laird et al. | |
| 6,333,155 B1 | 12/2001 | Lockhart et al. | |
| 6,383,754 B1 | 5/2002 | Kaufman et al. | |
| 6,509,160 B1 | 1/2003 | Sapolsky et al. | |
| 6,514,698 B1 | 2/2003 | Lopez et al. | |
| 6,562,569 B1 | 5/2003 | Dale | |
| 6,582,908 B2 | 6/2003 | Fodor et al. | |
| 6,605,432 B1 * | 8/2003 | Huang | 435/6 |
| 6,613,511 B1 | 9/2003 | Schmidt et al. | |
| 6,649,347 B2 | 11/2003 | Luo et al. | |
| 6,677,121 B2 | 1/2004 | Lizardi et al. | |
| 6,713,258 B2 | 3/2004 | Kilian | |
| 6,858,388 B2 | 2/2005 | Markowitz et al. | |
| 6,884,586 B2 | 4/2005 | Van Ness et al. | |
| 6,916,621 B2 * | 7/2005 | Shah | 435/6 |
| 6,936,419 B1 | 8/2005 | Berlin | |
| 6,958,217 B2 | 10/2005 | Pedersen et al. | |
| 6,960,436 B2 | 11/2005 | Cottrell | |
| 6,964,847 B1 | 11/2005 | Englert | |
| 6,979,728 B2 * | 12/2005 | Bradley et al. | 536/23.1 |
| 7,108,976 B2 | 9/2006 | Jones et al. | |
| 7,112,404 B2 | 9/2006 | Laird et al. | |
| 7,118,868 B2 | 10/2006 | Berlin | |
| 7,132,240 B2 | 11/2006 | Luo et al. | |
| 7,144,701 B2 | 12/2006 | Huang | |
| 7,153,671 B2 | 12/2006 | Berlin | |
| 7,186,512 B2 * | 3/2007 | Martienssen et al. | 435/6 |
| 7,195,870 B2 | 3/2007 | Olek et al. | |
| 7,214,485 B2 | 5/2007 | Belinsky | |
| 7,229,759 B2 | 6/2007 | Olek et al. | |
| 7,247,428 B2 | 7/2007 | Makrigiorgos et al. | |
| 7,285,394 B2 | 10/2007 | Lofton-Day et al. | |
| 7,368,239 B2 | 5/2008 | Zon | |
| 7,405,040 B2 | 7/2008 | Olek et al. | |
| 7,407,749 B2 | 8/2008 | Berlin et al. | |
| 7,425,415 B2 | 9/2008 | Pfeifer et al. | |

(Continued)

FOREIGN PATENT DOCUMENTS

EP 1344832 9/2003

(Continued)

OTHER PUBLICATIONS

Herman et al., Methylation-specific PCR: a novel PCR assay for methylation status of CpG islands PNAS 93(18): 9821-9826 (1996).*
Huang et al., Methylation profiling of CpG islands in human breast cancer cells. Human Molecular Genetics 8 (3) :459-470 (1999).*
Eads et al., MethyLight: a high-throughput assay to measure DNA methylation. Nucleic Acids Research 28(8) : e32 (2000).*
Yan et al., CpG island arrays: an application toward deciphering epigenetic signatures of breast cancer. Clinical Cancer Research 6(4): 1432-8 (2000).*
Hatada et al. A microarray-based method for detecting methylated loci. Journal of Human Genetics, 47(8) : 448-51(2002).*
Liang et al., Identification of DNA methylation differences during tumorigenesis by methylation-sensitive arbitrarily primed polymerase chain reaction. Methods 27(2) : 150-155 (2002).*
Wei et al., Methylation microarray analysis of late-stage ovarian carcinomas distinguishes progression-free survival in patients and identifies candidate epigenetic markers. Clinical Cancer Research 8(7) : 2246-2252(2002).*
Adorjan et al., Tumour class prediction and discovery by microarray-based DNA methylation analysis. Nucleic Acids Research 30 (5) :e21/1-e21/9 (2002).*

(Continued)

Primary Examiner — Ethan Whisenant
(74) Attorney, Agent, or Firm — Thomas J. Siepmann

(57) ABSTRACT

Arrays for genome-wide analysis of methylation are disclosed. In a preferred aspect arrays comprising a plurality of probes complementary to a plurality of identified CpG islands in the human, mouse and rat genome are disclosed. The arrays may be used to detect methylation within CpG islands in samples from human, mouse and rat genomes.

9 Claims, 5 Drawing Sheets

U.S. PATENT DOCUMENTS

| | | | |
|---|---|---|---|
| 7,524,629 B2 | 4/2009 | Olek et al. | |
| 7,611,869 B2 | 11/2009 | Fan | |
| 7,781,161 B2 | 8/2010 | Sidransky | |
| 7,794,929 B2 | 9/2010 | Baylin et al. | |
| 2001/0046669 A1 | 11/2001 | McCobmie et al. | |
| 2001/0053519 A1* | 12/2001 | Fodor et al. | 435/6 |
| 2002/0137086 A1 | 9/2002 | Olek et al. | |
| 2002/0197639 A1 | 12/2002 | Shia et al. | |
| 2003/0036081 A1 | 2/2003 | Adorjan et al. | |
| 2003/0096289 A1 | 5/2003 | Suzuki et al. | |
| 2003/0099997 A1 | 5/2003 | Bestor | |
| 2003/0104464 A1 | 6/2003 | Berlin et al. | |
| 2003/0143606 A1 | 7/2003 | Olek et al. | |
| 2003/0148326 A1 | 8/2003 | Olek et al. | |
| 2003/0148327 A1 | 8/2003 | Olek et al. | |
| 2003/0152950 A1 | 8/2003 | Garner et al. | |
| 2003/0157510 A1 | 8/2003 | Olek | |
| 2003/0162194 A1 | 8/2003 | Olek et al. | |
| 2003/0170689 A1 | 9/2003 | Stamatoyannapoulos et al. | |
| 2003/0175908 A1 | 9/2003 | Linnarsson et al. | |
| 2003/0212455 A1 | 11/2003 | Van Steensel et al. | |
| 2003/0215842 A1 | 11/2003 | Sledziewski et al. | |
| 2004/0023230 A1 | 2/2004 | Olek et al. | |
| 2004/0029128 A1 | 2/2004 | Cottrell et al. | |
| 2004/0038254 A1 | 2/2004 | Peoples et al. | |
| 2004/0048275 A1 | 3/2004 | Guldberg | |
| 2004/0072197 A1 | 4/2004 | Jones et al. | |
| 2004/0077074 A1* | 4/2004 | Ackley et al. | 435/287.2 |
| 2004/0086944 A1 | 5/2004 | Grigg et al. | |
| 2004/0102905 A1 | 5/2004 | Adorjan et al. | |
| 2004/0146868 A1 | 7/2004 | Cottrell et al. | |
| 2004/0203048 A1 | 10/2004 | Tran | |
| 2004/0234960 A1 | 11/2004 | Olek et al. | |
| 2004/0248090 A1 | 12/2004 | Olek et al. | |
| 2004/0248171 A1 | 12/2004 | Palmisano | |
| 2005/0009059 A1 | 1/2005 | Shapero et al. | |
| 2005/0021240 A1 | 1/2005 | Berlin et al. | |
| 2005/0064428 A1 | 3/2005 | Berlin | |
| 2005/0196792 A1 | 9/2005 | Fodor et al. | |
| 2005/0227230 A1 | 10/2005 | Carroll | |
| 2005/0233340 A1 | 10/2005 | Barrett | |
| 2005/0282157 A1 | 12/2005 | Olek | |
| 2006/0110741 A1 | 5/2006 | Asai | |
| 2006/0134650 A1 | 6/2006 | Gunderson | |
| 2006/0183115 A1 | 8/2006 | Wang | |
| 2006/0188986 A1 | 8/2006 | Millar | |
| 2009/0023137 A1* | 1/2009 | Van Der Zee et al. | 435/6 |

FOREIGN PATENT DOCUMENTS

| | | |
|---|---|---|
| EP | 1312685 | 11/2003 |
| EP | 1362929 | 11/2003 |
| EP | 1568786 | 8/2005 |
| WO | WO 00/26401 | 5/2000 |
| WO | WO 01/38565 | 5/2001 |
| WO | WO 01/77377 | 10/2001 |
| WO | WO 02/00927 | 1/2002 |
| WO | WO 02/04686 | 1/2002 |
| WO | WO 02/18649 | 3/2002 |
| WO | WO 02/34942 | 5/2002 |
| WO | WO 02/083705 | 10/2002 |
| WO | WO 03/023065 | 3/2003 |
| WO | WO 03/025215 | 3/2003 |
| WO | WO 03/027259 | 4/2003 |
| WO | WO 03/048732 | 6/2003 |
| WO | WO 03/064682 | 8/2003 |
| WO | WO 03/076666 | 9/2003 |
| WO | WO 03/080862 | 10/2003 |
| WO | WO 03/087774 | 10/2003 |
| WO | WO 2004/048555 | 6/2004 |
| WO | WO 2004/096825 | 11/2004 |
| WO | WO 2005/021778 | 3/2005 |
| WO | WO 2005/021802 | 3/2005 |
| WO | WO 2005/033332 | 4/2005 |

OTHER PUBLICATIONS

Chen et al., Methylation target array for rapid analysis of CpG island hypermethylation in multiple tissue genomes. Am. J. of Pathology 163 (1) : 37-45 (2003).*

Yan et al., Dissecting complex epigenetic alterations in breast cancer using CpG island microarrays. Cancer Research 61 : 8375-8380 (2001).*

Adorjan et al., "Tumour class prediction and discovery by microarray-based DNA methylation analysis," *Nucleic Acids Research*, 30(5):e21/1-e21/9 (2002).

Bernstein et al., "Genomic maps and comparative analysis of histone modifications in human and mouse," *Cell*, 120(2):169-81 (Jan. 2005).

Chen et al., "Methylation target array for rapid analysis of CpG island hypermethylation in multiple tissue genomes," *Am. J. of Pathology*, 163(1):37-45 (2003).

Eads et al., "MethyLight: a high-throughput assay to measure DNA methylation," *Nucleic Acids Research*, 28(8):e32 (2000).

Faruqi et al., "High-throughput genotyping of single nucleotide polymorphisms with rolling circle amplification," *BMC Genomics*, 2:4 (2001).

Frigola et al., "Differential DNA hypermethylation and hypomethylation signatures in colorectal cancer," *Human Molecular Genetics*, 2005, pp. 319-326, vol. 14, No. 2, Oxford University Press.

Frigola et al., "Methylome profiling of cancer cells by amplification of inter-methylated sites (AIMS)," *Nucleic Acids Research*, 2002, vol. 30, No. 7, e28.

Gao et al., "DNA microarray: a high throughput approach for methylation detection," *Colloids and Surfaces B: Biointerfaces*, 2005, pp. 127-131, vol. 40, No. 3, Elsevier.

Gitan et al., "Methylation-Specific Oligonucleotide Microarray: A New Potential for High-Throughput Methylation Analysis," *Genome Research*, 2002, pp. 158-164, vol. 12, Issue 1, Cold Spring Harbor Laboratory Press.

Hatada et al., "A microarray-based method for detecting methylated loci," *Journal of Human Genetics*, 47(8):448-51 (2002).

Herman et al., "Methylation-specific PCR: a novel PCR assay for methylation status of CpG islands," *PNAS* 93(18):9821-9826 (1996).

Hirschhorn et al., "SBE-TAGS: An array-based method for efficient single-nucleotide genotyping," PNAS 97(22):12164-12169 (2000).

Huang et al., Methylation profiling of CpG islands in human breast cancer cells. Human Molecular Genetics 8 (3): 459-470 (1999).

Larijani et al., "Methylation protects cytidines from AID-mediated deamination," *Molecular Immunology*, 2005, pp. 599-604, vol. 42, Elsevier.

Liang et al., "Identification of DNA methylation differences during tumorigenesis by methylation-sensitive arbitrarily primed polymerase chain reaction," *Methods*, 27(2):150-155 (2002).

Lipshutz et al., "High density synthetic oligonucleotide arrays," *Nature Genetics Supplement*, vol. 21, pp. 20-24 (Jan. 1999).

Oakeley, "DNA Methylation Analysis: A Review of Current Methodologies," *Pharmacology & Therapeutics*, 1999, pp. 389-400, vol. 84.

Rauch et al., "Methylated-CpG island recovery assay: a new technique for the rapid detection of methylated-CpG islands in cancer," *Laboratory Investigation*, 2005, pp. 1-9.

Robinson et al., "Stable methylation patterns in interspecific antelope hybrids and the characterization and localization of a satellite fraction in the *Alcelaphini* and *Hippotragini*," *Chromosome Research*, 8(7):635-643 (Oct. 2000).

Sadri et al., "Rapid analysis of DNA methylation using new restriction enzyme sites created by bisulfite modification," *Nucleic Acids Research*, 1996, pp. 5058-5059, vol. 24, No. 24, Oxford University Press.

Shi et al., "Expressed CpG Island Sequence Tag Microarray for Dual Screening of DNA Hypermethylation and Gene Silencing in Cancer Cells," *Cancer Research*, 62:3214-3220 (Jun. 2002).

Thomassin et al., "MethylQuant: a sensitive method for quantifying methylation of specific cytosines within the genome," *Nucleic Acids Research*, 2004, vol. 32, No. 21, e168, Oxford University Press.

Tompa et al., "Genome-Wide Profiling of DNA Methylation Reveals Transposon Targets of Chromomethylase3," *Current Biology*, Jan. 8, 2002, pp. 65-68, vol. 12. Elseveir.

Wei et al., "Methylation microarray analysis of late-stage ovarian carcinomas distinguishes progression-free survival in patients and identifies candidate epigenetic markers," *Clinical Cancer Research*, 8(7):2246-2252 (2002).

Xiong et al., "COBRA: a sensitive and quantitative DNA methylation assay," *Nucleic Acids Res.*, 25(1):2532-4 (Jun. 1997).

Yan et al., "Applications of CpG island microarrays for high-throughput analysis of DNA methylation," *J. Nutr.*, 132(8 Suppl): 2430S-2434S (Aug. 2002).

Yan et al., "CpG island arrays: an application toward deciphering epigenetic signatures of breast cancer," *Clinical Cancer Research*, 6(4):1432-8 (2000).

Yan et al., "Dissecting complex epigenetic alterations in breast cancer using CpG island microarrays," *Cancer Research*, 61:8375-8380 (2001).

Yan et al., "Use of CpG island microarrays to identify colorectal tumors with a high degree of concurrent methylation," *Methods*, 27(2):162-9 (Jun. 2002).

* cited by examiner

ANALYSIS OF METHYLATION USING NUCLEIC ACID ARRAYS

RELATED APPLICATIONS

The present application claims priority to U.S. Provisional Application No. 60/788,520, filed Mar. 31, 2006, the entire disclosure of which is incorporated herein by reference.

FIELD OF THE INVENTION

The present invention relates to arrays and methods for detecting methylation of nucleic acids.

REFERENCE TO SEQUENCE LISTING

The Sequence Listing submitted on compact disk is hereby incorporated by reference. The file on the disk is named 3791.1sequencelist.txt, the file is 108 MB and the date of creation is Mar. 30, 2007.

BACKGROUND OF THE INVENTION

The genomes of higher eukaryotes contain the modified nucleoside 5-methyl cytosine (5-meC). This modification is usually found as part of the dinucleotide CpG. Cytosine is converted to 5-methylcytosine in a reaction that involves flipping a target cytosine out of an intact double helix and transfer of a methyl group from S-adenosylmethionine by a methyltransferase enzyme (Klimasauskas et al., *Cell* 76:357-369, 1994). This enzymatic conversion is the only epigenetic modification of DNA known to exist in vertebrates and is essential for normal embryonic development (Bird, *Cell* 70:5-8, 1992; Laird and Jaenisch, *Human Mol. Genet.* 3:1487-1495, 1994; and Li et al., *Cell* 69:915-926, 1992).

The frequency of the CpG dinucleotide in the human genome is only about 20% of the statistically expected frequency, possibly because of spontaneous deamination of 5-meC to T (Schoreret et al., *Proc. Natl. Acad Sci. USA* 89:957-961, 1992). There are about 28 million CpG doublets in a haploid copy of the human genome and it is estimated that about 70-80% of the cytosines at CpGs are methylated. Regions where CpG is present at levels that are approximately the expected frequency are referred to as "CpG islands" (Bird, A. P., *Nature* 321:209-213, 1986). These regions have been estimated to comprise about 1% of vertebrate genomes and account for about 15% of the total number of CpG dinucleotides. CpG islands are typically between 0.2 and 1 kb in length and are often located upstream of housekeeping and tissue-specific genes. CpG islands are often located upstream of transcribed regions, but may also extend into transcribed regions. About 2-4% of cytosines are methylated and probably the majority of cytosines that are 5' of Gs are methylated. Most of the randomly distributed CpGs are methylated, but only about 20% of the CpGs in CpG islands are methylated.

DNA methylation is an epigenetic determinant of gene expression. Patterns of CpG methylation are heritable, tissue specific, and correlate with gene expression. The consequence of methylation is usually gene silencing. DNA methylation also correlates with other cellular processes including embryonic development, chromatin structure, genomic imprinting, somatic X-chromosome inactivation in females, inhibition of transcription and transposition of foreign DNA and timing of DNA replication. When a gene is highly methylated it is less likely to be expressed, possibly because CpG methylation prevents transcription factors from recognizing their cognate binding sites. Proteins that bind methylated DNA may also recruit histone deacetylase to condense adjacent chromatin. Such "closed" chromatin structures prevent binding of transcription factors. Thus the identification of sites in the genome containing 5-meC is important in understanding cell-type specific programs of gene expression and how gene expression profiles are altered during both normal development and diseases such as cancer. Precise mapping of DNA methylation patterns in CpG islands has become essential for understanding diverse biological processes such as the regulation of imprinted genes, X chromosome inactivation, and tumor suppressor gene silencing in human cancer caused by increase methylation.

Methylation of cytosine residues in DNA plays an important role in gene regulation. Methylation of cytosine may lead to decreased gene expression by, for example, disruption of local chromatin structure, inhibition of transcription factor-DNA binding, or by recruitment of proteins which interact specifically with methylated sequences and prevent transcription factor binding. DNA methylation is required for normal embryonic development and changes in methylation are often associated with disease. Genomic imprinting, X chromosome inactivation, chromatin modification, and silencing of endogenous retroviruses all depend on establishing and maintaining proper methylation patterns. Abnormal methylation is a hallmark of cancer cells and silencing of tumor suppressor genes is thought to contribute to carcinogenesis. Methylation mapping using microarray-based approaches may be used, for example, to profile cancer cells revealing a pattern of DNA methylation that may be used, for example, to diagnose a malignancy, predict treatment outcome or monitor progression of disease. Methylation in eukaryotes can also function to inhibit the activity of viruses and transposons, see Jones et al., *EMBO J.* 17:6385-6393 (1998). Alterations in the normal methylation process have also been shown to be associated with genomic instability (Lengauer et al., *Proc. Natl. Acad. Sci. USA* 94:2545-2550, 1997). Such abnormal epigenetic changes may be found in many types of cancer and can serve as potential markers for oncogenic transformation.

SUMMARY OF THE INVENTION

The present invention provides methods and arrays for analysis of methylation status of sites in genomic DNA.

In a first aspect, the invention thus provides an array of more than 250,000 different sequence probes that are complementary to regions of the human genome that are rich in CpG dinucleotides.

In one embodiment the array comprises probes to more than 25,000 CpG islands in the human genome. The islands are selected from annotated islands in public databases, preferably the UCSC genome browser. In preferred aspects islands are selected that have a GC content of 50% or greater over a length of 200 base pairs or greater.

In one embodiment the array comprises at least one probe set for each CpG island to be interrogated and each probe set comprises 8, 20 to 30 base probes that are perfectly complementary to a region of the CpG island over the entire length of the probe.

In another aspect, the array comprises three probes sets comprising 8 probes for each CpG island that is greater than 5 kb in length. The probe sets may be distributed so that the probes in one probe set are complementary to regions in the 5' approximately 1,700 base pairs, one the 3' 1,700 base pairs and one the central 1,700 base pairs of the island.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which.

Figure 1:
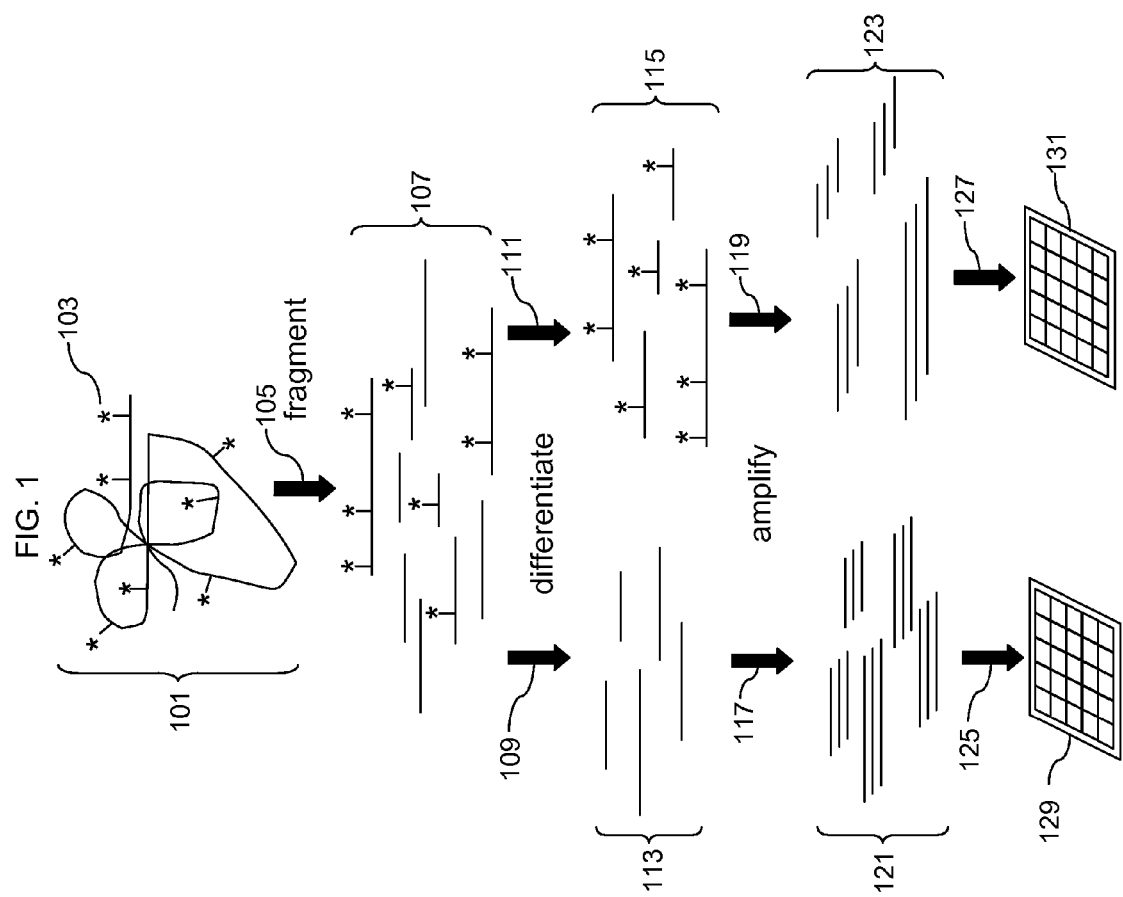
FIG. 1 is a schematic illustrating a method of analyzing the methylation status of genomic DNA.

DETAILED DESCRIPTION OF THE INVENTION a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being, but may also include other organisms including but not limited to mammals, plants, fungi, bacteria or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, N.Y., Gait, "*Oligonucleotide Synthesis: A Practical Approach*" 1984, IRL Press, London, Nelson and Cox (2000), *Lehninger, Principles of Biochemistry* 3$^{rd}$ Ed., W.H. Freeman Pub., New York, N.Y. and Berg et al. (2002) *Biochemistry*, 5$^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with hybridization to an array, the sample may be amplified by a variety of mechanisms, some of which may employ PCR. See, for example, *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159, 4,965,188, and 5,333,675. The sample may be amplified on the array. See, for example, U.S. Pat. No. 6,300,070 which is incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173

(1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245), rolling circle amplification (RCA) (for example, Fire and Xu, *PNAS* 92:4641 (1995) and Liu et al., *J. Am. Chem. Soc.* 118:1587 (1996)) and nucleic acid based sequence amplification (NABSA), (See, U.S. Pat. Nos. 5,409,818, 5,554,517, and 6,063,603). Other amplification methods that may be used are described in, U.S. Pat. Nos. 5,242,794, 5,494,810, 4,988,617 and in U.S. Ser. No. 09/854,317. Other amplification methods are also disclosed in Dahl et al., *Nuc. Acids Res.* 33(8):e71 (2005) and circle to circle amplification (C2CA) Dahl et al., PNAS 101:4548 (2004). Locus specific amplification and representative genome amplification methods may also be used.

Additional methods of sample preparation and techniques for reducing the complexity of a nucleic sample are described in Dong et al., *Genome Research* 11, 1418 (2001), in U.S. Pat. Nos. 6,872,529, 6,361,947, 6,391,592 and 6,107,023, US Patent Publication Nos. 20030096235 and 20030082543 and U.S. patent application Ser. No. 09/916,135.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davism, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. Nos. 10/389,194, 60/493,495 and in PCT Application PCT/US99/06097 (published as WO 99/47964), each of which also is hereby incorporated by reference in its entirety for all purposes. Instruments and software may also be purchased commercially from various sources, including Affymetrix.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., *Introduction to Computational Biology Methods* (PWS Publishing Company, Boston, 1997); Salzberg, Searles, Kasif, (Ed.), *Computational Methods in Molecular Biology,* (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

Methods for detection of methylation status are disclosed, for example, in Fraga and Esteller, *BioTechniques* 33:632-649 (2002) and Dahl and Guldberg Biogerontology 4:233-250 (2003). Methylation detection using bisulfite modification and target specific PCR have been disclosed, for example, in U.S. Pat. Nos. 5,786,146, 6,200,756, 6,143,504, 6,265,171, 6,251,594, 6,331,393, and 6,596,493. U.S. Pat. No. 6,884,586 disclosed methods for methylation analysis using nicking agents and isothermal amplification.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/197,621, 10/063,559 (United States Publication No. 20020183936), 10/065,856, 10/065,868, 10/328,818, 10/328,872, 10/423,403, and 60/482,389.

All documents, i.e., publications and patent applications, cited in this disclosure, including the foregoing, are incorporated by reference herein in their entireties for all purposes to the same extent as if each of the individual documents were specifically and individually indicated to be so incorporated by reference herein in its entirety.

b) Definitions

"Adaptor sequences" or "adaptors" or "linkers" are generally oligonucleotides of at least 5, 10, or 15 bases and preferably no more than 50 or 60 bases in length; however, they may be even longer, up to 100 or 200 bases that may be attached to the ends of fragments. Adaptor sequences may be synthesized using any methods known to those of skill in the art. For the purposes of this invention they may, as options, comprise primer binding sites, recognition sites for endonucleases, common sequences and promoters. The adaptor may be entirely or substantially double stranded or entirely single stranded. A double stranded adaptor may comprise two oligonucleotides that are at least partially complementary. The adaptor may be phosphorylated or unphosphorylated on one or both strands.

Adaptors may be ligated to blunt or sticky ends of fragments and the adaptors may have blunt or sticky ends. They may comprise a substantially double stranded region and a short single stranded region which is complementary to the single stranded region created by digestion with a restriction enzyme, also referred to as a "sticky end". Overhangs may also be converted to blunt ends by filling in an overhang or removing an overhang.

Methods of ligation will be known to those of skill in the art and are described, for example in Sambrook et at. (2001) and the New England BioLabs catalog Methods include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; E. coli DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'->5' phosphodiester bond, substrates include single-stranded RNA and DNA as well as dinucleoside pyrophosphates; or any other methods described in the art.

Adaptors may also incorporate modified nucleotides that modify the properties of the adaptor sequence. For example, phosphorothioate groups may be incorporated in one of the adaptor strands. A phosphorothioate group is a modified phosphate group with one of the oxygen atoms replaced by a sulfur atom. In a phosphorothioated oligo (often called an "S-Oligo", souse or ail of the internucleotide phosphate groups are replaced by phosphorothioate groups. The modified backbone of all S-Oligo is resistant to the action of most exonucleases and endonucleases. Phosphorothioates may be incorporated between all residues of an adaptor strand, or at specified locations within a sequence. A useful option is to sulfurize only the last few residues at each end of the oligo. This results in an oligo that is resistant to exonucleases, but has a natural DNA center.

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Perfectly complementary refers to 100% complementarity over the length of a sequence. For example, a 25 base probe is perfectly complementary to a target when all 25 bases of the probe are complementary to a contiguous 25 base sequence of the target with no mismatches between the probe and the target over the length of the probe.

The term "CpG island" as used herein refers to stretches of DNA in a genome that are rich in GC relative to the rest of the genome. Typically the GC content is 50% or greater in these regions which extend over hundreds of base pairs and sometimes thousands. Often these regions mark the 5' ends of genes.

The term "epigenetic" as used herein refers to factors other than the primary sequence of the genome that affect the development or function of an organism, they can affect the phenotype of an organism without changing the genotype. Epigenetic factors include modifications in gene expression that are controlled by heritable but potentially reversible changes in DNA methylation and chromatin structure. Methylation patterns are known to correlate with gene expression and in general highly methylated sequences are poorly expressed.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." Hybridizations are usually performed under stringent conditions, for example, at a salt concentration of no more than about 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations or conditions of 100 mM MES, 1 M [Na$^+$], 20 mM EDTA, 0.01% Tween-20 and a temperature of 30-50° C., preferably at about 45-50° C. Hybridizations may be performed in the presence of agents such as herring sperm DNA at about 0.1 mg/ml, acetylated BSA at about 0.5 mg/ml. As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GeneChip Mapping Assay Manual, 2004, available at Affymetrix.com.

The term "hybridization probes" as used herein are oligonucleotides capable of binding in a base-specific manner to a complementary strand of nucleic acid. Such probes include peptide nucleic acids, as described in Nielsen et al., *Science*

254, 1497-1500 (1991), LNAs, as described in Koshkin et al. *Tetrahedron* 54:3607-3630, 1998, and U.S. Pat. No. 6,268,490 and other nucleic acid analogs and nucleic acid mimetics.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "label" as used herein refers to a luminescent label, a light scattering label, a radioactive label or a molecule that interacts with a detectable label. Fluorescent labels include the commercially available fluorescein phosphoramidites such as Fluoreprime (Pharmacia), Fluoredite (Millipore) and FAM (ABI). See U.S. Pat. No. 6,287,778. In preferred aspects biotin is incorporated into nucleic acids and is used to detectably label the nucleic acids through interaction with streptavidin.

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

Restriction enzymes or restriction endonucleases and their properties are well known in the art. A wide variety of restriction enzymes are commercially available, from, for example, New England Biolabs. Restriction enzymes recognize a sequence specific sites (recognition site) in DNA. Typically the recognition site varies from enzyme to enzyme and may also vary in length. Isoschizomers are enzymes that share the same recognition site. Restriction enzymes may cleave close to or within their recognition site or outside of the recognition site. Often the recognition site is symmetric because the enzyme binds the double stranded DNA as homodimers. Recognition sequences may be continuous or may be discontinuous, for example, two half sites separated by a variable region. Cleavage can generate blunt ends or short single stranded overhangs.

In preferred aspects of the present invention enzymes that include at least one CpG dinucleotide in the recognition site may be used. Enzymes with a recognition site that includes the sequence CCGG include, for example, Msp I, Hpa II, Age I, Xma I, Sma I, NgoM IV, Nae I, and BspE I. Enzymes with a recognition site that includes the sequence CGCG include, for example, BstU I, Mlu I, Sac II, BssH II and Nru I. Enzymes with a recognition site that includes the sequence GCGC include, for example, Hin P1 I, Hha I, Afe I, Kas I, Nar I, Sfo I, Bbe I, and Fsp I. Enzymes with a recognition site that includes the sequence TCGA include, for example, Taq I, Cla I, BspD I, PaeR7 I, Tli I, Xho I, Sal I, and BstB I. For additional enzymes that contain CpG in the recognition sequence. See, for example, the New England Biolabs catalog and web site. In some aspects two restriction enzymes may have a different recognition sequence but generate identical overhangs or compatible cohesive ends. For example, the overhangs generated by cleavage with Hpa II or Msp I can be ligated to the overhang generated by cleavage with Taq I. Some restriction enzymes that include CpG in the recognition site are unable to cleave if the site is methylated, these are methylation sensitive. Other enzymes that contain CpG in their recognition site can cleave regardless of the presence of methylation, these are methylation insensitive. Examples of methylation insensitive enzymes, that include a CpG in the recognition site, include BsaW I (WCCGGW), BsoB I, BssS I, Msp I, and Taq I. Examples of methylation sensitive enzymes, that include a CpG in the recognition site, include Aat II, Aci I, Acl I, Afe I, Age I, Asc I, Ava I, BmgB I, BsaA I, BsaH I, BspD I, Eag I, Fse I, Fau I, Hpa II, HinP1 I, Nar I, and SnaB I.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

The term "tags" or "barcode tags" is used herein to refer to short nucleic acids sequence of, for example, 15 to 50 bases, that may be used to mark a molecule or mixture of interest. They are preferably part of a set of tags that function together as detectable markers that share common hybridization properties and are not found naturally in the molecule or mixture of interest. In preferred aspects tags are selected from random sequences of the same length that are not found in a genome of interest, for example, 20 mers not found in the human genome, and have similar melting temperatures from their respective tag probes which are the perfect complement of the tags. They may be designed algorithmically to maximize discrimination on a microarray displaying complements of the respective tags; a 1:1 correspondence as between tag sequence and nucleic acid to which it is appended permits each such nucleic acid to be identified by detection of the bar code uniquely associated therewith. See, e.g., Shoemaker et al., *Nature Genet.* 14(4):450-6 (1996); EP 0799897; Fan et al., *Genome Res.* 10:853-60 (2000); and U.S. Pat. No. 6,150,516, the disclosures of which are incorporated herein by reference in their entireties.

CpG Island Arrays

Mammalian methylation patterns are complex and change during development, see van Steensel and Henikoff *BioTechniques* 35: 346-357 (2003). Methylation in promoter regions is generally accompanied by gene silencing and loss of methylation or loss of the proteins that bind to the methylated CpG can lead to diseases in humans, for example, Immunodeficiency Craniofacial Syndrome and Rett Syndrome, Bestor (2000) *Hum. Mol. Genet.* 9:2395-2402. DNA methylation may be gene-specific and occurs genome-wide.

Methods for detecting methylation status have been described in, for example U.S. Pat. Nos. 6,214,556, 5,786,146, 6,017,704, 6,265,171, 6,200,756, 6,251,594, 5,912,147, 6,331,393, 6,605,432, and 6,300,071 and US Patent Application publication Nos. 20030148327, 20030148326, 20030143606, 20030082609 and 20050009059, each of which are incorporated herein by reference. Other array based methods of methylation analysis are disclosed in U.S. patent application Ser. Nos. 11/058,566 (Pg Pub 20050196792 A1) and 11/213,273 (PgPub 20060292585 A1), which are both incorporated herein by reference in their entireties. For a review of some methylation detection methods, see, Oakeley, E. J., *Pharmacology & Therapeutics* 84:389-400 (1999). Available methods include, but are not limited to: reverse-phase HPLC, thin-layer chromatography, SssI methyltransferases with incorporation of labeled methyl groups, the chloracetaldehyde reaction, differentially sensitive restriction enzymes, hydrazine or permanganate treatment (m5C is cleaved by permanganate treatment but not by hydrazine treatment), sodium bisulfite, combined bisulphate-restriction analysis, and methylation sensitive single nucleotide primer extension.

Aberrant DNA methylation at CpG islands has been proven to play an important role in the development of cancer. Genome-wide monitoring of alterations in DNA methylation patterns will lead to new insights into the early epigenetic events of tumor genesis and the discovery of biomarkers for cancer. CpG island microarrays to interrogate the vast majority of CpG islands found in the genome and methods of using CpG island microarrays are disclosed herein. The CpG island microarrays may be used for rapid screening and high-throughput, genome-wide surveys of DNA methylation status in, for example, mouse, human and rat. The array design strategy, examples of detecting DNA methylation and data analysis methods are disclosed. A promoter tiling array may also be used as a complementary method for methylation detection in human promoter regions. A promoter tiling array with over 25,000 promoters from human genes is also discussed. The microarray technology disclosed herein may be used, for example, for methylation research and biomarker discovery.

In a preferred aspect arrays containing probes that are selected to interrogate regions that are candidates for methylation and for regulation by methylation are disclosed. Some embodiments are defined with reference to the sequence listing that has been incorporated herein by reference. The sequence listing contains the sequences of 743,256 probes. Each sequence in the sequence listing represents the sequence of a probe that may be present on a CpG island array. The sequences include a plurality of experimental probe sequences and a plurality of control probe sequences. The experimental probe sequences are SEQ ID NO. 1-668,564 and the control sequences are SEQ ID NO. 668,565-743,256. Approximately 90% of the probes of the array are experimental probes with approximately 10% of the probes as control probes.

The sequence listing contains experimental and control probes for human, mouse and rat arrays. The experimental human probes are SEQ ID NO. 1-222,822. The experimental mouse probes are SEQ ID NO. 222,823-448,233. The experimental rat probes are SEQ ID NO. 448,234-668,564. The human control probes are SEQ ID NO. 668,565-693,466. The mouse control probes are SEQ ID NO. 693,467-715,779. The rat control probes are SEQ ID NO. 715,780-743,256.

In one aspect an array for analysis of methylation in humans is disclosed. The array may comprise a plurality of experimental probes selected from the probes represented by SEQ ID NO. 1-222,822. The array may further comprise control probes selected from the control probes represented by SEQ ID NO. 668,565-693,466.

In another aspect an array for analysis of methylation in rat is disclosed. The array may comprise a plurality of experimental probes selected from the probes represented by 448, 234-668,564. The array may further comprise control probes selected from the control probes represented by SEQ ID NO. 715,780-743,256.

In another aspect an array for analysis of methylation in mouse is disclosed. The array may comprise a plurality of experimental probes selected from the probes represented by SEQ ID NO. 222,823-448,233. The array may further comprise control probes selected from the control probes represented by SEQ ID NO. 693,467-715,779.

It should be understood that while the probes of an array may be selected to be perfectly complementary to the sequence of a selected organisms, for example, human, mouse or rat, that the array may be useful for hybridization to related species that share sequence homology. For example, an array designed to be complementary to human genetic material may be used to analyze a sample from another primate, for example, gorilla.

In preferred aspects the arrays contain more than 200,000 probes that are perfectly complementary to regions of the genome that are predicted to be CpG islands. The probes are preferably between 15 and 100 bases, more preferably between 20 and 50 bases and most preferably between 20 and 30 bases. In one aspect more than 90% of the probes are 25 bases in length. Probes are arranged on the array so that each different sequence is present in a distinct feature or geographical location of the array and that location is known or determinable. Not all probes within a feature area need be full length.

In some aspects CpG island arrays may vary from other arrays in the frequency of CG dinucleotides in the probes. Since the CG dinucleotide occurs at a relatively low frequency, genome arrays such as expression arrays or genotyping arrays typically have lower frequency of CG in the probes. In one aspect more than 80, 85, 90 or 95% of the probes of the array contain at least one CG dinucleotide. In preferred aspects more than 50, 60, 70 or 80% of the probes of the array contain at least two CG dinucleotides. A CG dinucleotide is a 5'-CG-3' where the G and C are contiguous in the nucleic acid chain and not separated by another nucleotide. In one aspect at least 25% of the experimental probes have at least 3 GC dinucleotides. In one aspect at least 7.5% of the experimental probes of the array have 4 or more GC dinucleotides. In preferred aspects there are more than 100,000, 250,000, 500, 000, 750,000, 1,000,000, or 2,000,000 experimental probes on the array.

In one embodiment, probes are selected for the array so that for each CpG island that is less than 5 kb the array includes a probe set of 8 probes that target that island. For islands greater than 5 kb 3 probe sets of 8 probes each were designed and included on the array. The 3 probes sets were spaced roughly so that one interrogated the 3' region of the island, one the middle and one the 5' region. If, for example, the island is of length 6 kb a first probes set may be designed to bases 1-2000, a second to bases 2001-4000 and a third to bases 4001-6000 of the island.

In one embodiment all of the probes in a probe set are selected to be within the same 1600 base pair or smaller region. This increases the likelihood that all probes in a probe set are on a common restriction fragment in a methylation assay.

In a preferred aspect, probe selection for islands that are greater than 1 kb and less than 5 kb, begins in the central 1 kb of the island. For islands greater than 5 kb, probe selection of a first probe set may start within the central 1 kb of the fragments, the 3'-most 1 kb for a second probe set and the 5'-most 1 kb for a third probe set.

In one embodiment the quality of a selected probe set may be evaluated after selection by assessing a probe set score. For those islands that have a probe set score of less than 1.44 (probe set score is 0.18×the number of probes), the probe selection region may be extended by 150 bp at either end (300 bases overall) and probe selection is repeated. All _x sets were automatically failed and failed probe sets were not rescue based on an average raw probe score. For regions that failed a second round of probe selection the region may be further extended by 150 bp on either end and probe selection can be repeated. In one embodiment probe sets that are subjected to a third round of probe selection may be allowed to have fewer probes, for example, 5-8 probes per set.

In one embodiment, during probe selection, probes may be pruned versus the repeat database 'Repbase', and pruned versus the islands themselves +/−500 bp of genomic sequence, and the *Arabidopsis* mRNA clones. This eliminates or minimizes crosshybridization to repeats, and reduces cross hybridization between islands, such that the signal detected should be specific to a given island.

In a preferred embodiment the array is a 400 format array with features that are about 5 microns by 5 microns. Increased or decreased array and feature sizes may be used, for example, array format may be 49, 100, 700 or 900 format and the feature size may be 1×1, 7×7, 11×11, or 18×18 microns. Smaller and larger feature sizes or a mixture of the above feature sizes may also be used. In a preferred aspect the 400 format arrays with 5 micron feature size have about 250,000 different features. Each feature may be a different probe. Some probes may be present in more than a single feature. In a preferred aspect plus strand perfect match probes are used. Controls may be GC matched antigenomic controls (about 2600 probes at 100 probes per bin—each bin is a different GC content). Additional controls may include, for example, *Arabidopsis* genomic controls and *Pseudomonal* genomic sequences. Controls may be selected to have GC content that is similar to the target sequences. In one aspect probes to well characterized genes that are known to be associated with cancer may be included on the array. In one aspect probes to ten or more human genes that are known to be associated with cancer may be included on the array. Probes to repetitive sequence and to 18S and 28S ribosomal RNA genes may also be included.

In one aspect probe sets are included for genes that are known to be regulated by methylation. In one aspect a set of 15 genes was selected, and the orthologs of these from each species (when available) were tiled as 40-probe (perfect match-only) sets. Probes for 14 human genes (16 CpG islands), 13 mouse (13 CpG islands), and 11 rat genes (11 CpG islands), were tiled. The gene names and the location of the CpG island associated with that gene, if any, are shown in table 1.

| Human | Mouse | Rat |
|---|---|---|
| CDKN2A chr9: 21964579-21965306 | Cdkn2a chr4: 88280326-88281746 | Cdkn2a chr5: 108916025-108916249 |
| CDKN2A chr9: 21984102-21985910 | Mgmt chr7: 131261988-131262200 | Mgmt chr1: 196779125-196779347 |
| MGMT chr10: 131154939-131155700 | Mlh1 chrX: 87947039-87947267 | Mlh1 chr8: 115672549-115673779 |
| MLH1 chr3: 37009233-37010360 | Gstp1 chr19: 3826567-3826865 | Gstp1 chr1: 206783223-206783432 |
| GSTP1 chr11: 67107505-67108529 | Brca1 chr11: 101372865-101373065 | Brca1 chr10: 90586958-90587201 |
| BRCA1 chr17: 38531661-38531986 | Cdh1 chr8: 105898932-105899662 | Cdh1 chr19: 36447500-36448076 |
| CDH1 chr16: 67328536-67329845 | Timp3 chr10: 86260784-86261356 | Timp3 chr7: 19736510-19737381 |
| TIMP3 chr22: 31521935-31522821 | Dapk1 chr13: 59260184-59261075 | Dapk1 chr17: 9778756-9779643 |
| DAPK1 chr9: 87342069-87343371 | Rassf1 chr9: 107619881-107620907 | Rassf1 chr8: 112821629-112822624 |
| RASSF1 chr3: 50349269-50350633 | Thbs1 No CpG Island | Thbs1 No CpG island |
| RASSF1 chr3: 50352808-50353544 | Rarb chr14: 15071137-15071693 | Rarb chr15_random: 195605-195857 |
| THBS1 chr15: 37659820-37660859 | Trp73 chr4: 152632046-152632968 | |
| RARB No CpG Island | Stk11 chr10: 80238679-80240278 | |
| TP73 chr1: 3589603-3592793 | Apc chr18: 34443822-34444584 | |

In a preferred aspect the arrays are used to analyze a sample that has been treated to differentiate between methylated and unmethylated sequences. Methylation is an epigenetic modification of DNA and information about methylation is typically lost during most methods of nucleic acid amplification such as PCR, random or semi-random priming based amplification, or locus specific primer extension based amplification. To identify regions that were methylated in a starting sample methods, such as the method shown in FIG. 1, may be used that enrich for methylated sequences relative to unmethylated prior to or during amplification, and those enriched sequences may be detected by hybridization to an array such as those arrays disclosed herein.

In FIG. 1 the genomic DNA 101 with methylation sites 103 marked by an (*) is fragmented in step 105, for example, by restriction digestion, shearing, nebulization, sonication, or endonuclease treatment. A mixture 107 of methylated (marked with *) and unmethylated fragments is obtained. Aliquots of the mixture 107 may be treated differentially in steps 109 and 111 to enrich for methylated fragments in step 109 or unmethylated fragments in step 111. Step 109 generates a sample 113 that is enriched for unmethylated fragments and step 111 generates a sample 115 that is enriched for methylated fragments. The enriched fragments are amplified in steps 117 and 119 to generate amplified samples 121 and 123. Amplification does not preserve methylation but amplification product 121 is enriched for sequences that were not methylated in 101 and amplification product 123 is enriched for sequences that were methylated in 101. The enriched amplification products may be analyzed in steps 125 and 127 respectively by hybridization to arrays 129 and 131. In a preferred aspect arrays 129 and 131 are arrays where more than 50, 60, 70, 80 or 90% of the probes on the array are complementary to a region that contains at least one CpG dinucleotide.

Alternatively methods that enrich for regions that are unmethylated relative to regions that are methylated may also be used. Methods for separation of methylated from unmethylated nucleic acids have been described, see, for example, US Patent Publication Nos. 20010046669, 20030157546, and 20030180775 which are each incorporated herein by reference in their entireties.

Figure 2:
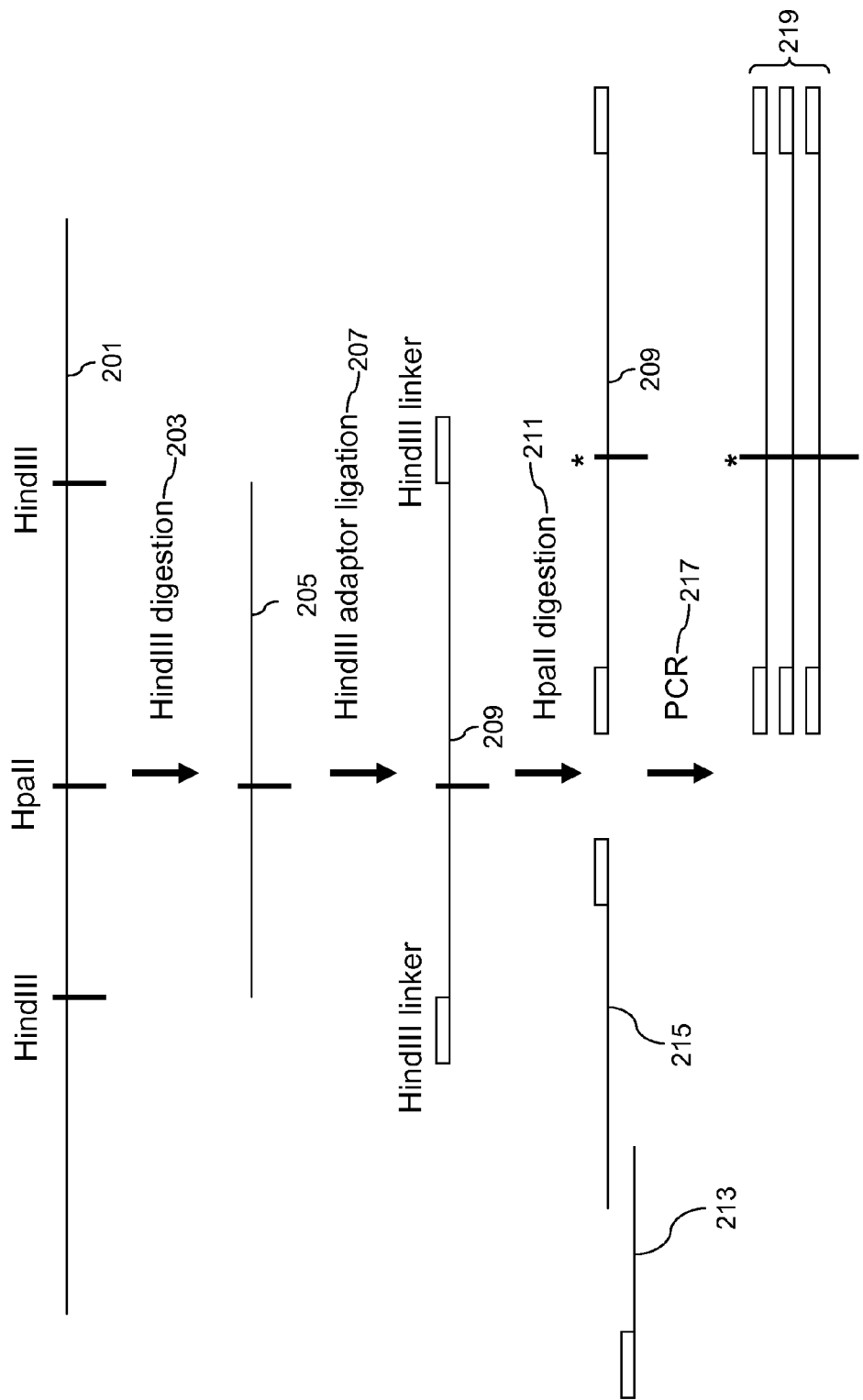
FIG. 2 is a schematic representation illustrating a method for enriching for DNA that is methylated.

In a particularly preferred aspect, illustrated schematically in FIG. 2, a genomic sample 201 is fragmented in step 203 by a method that is not sensitive to methylation, HindIII digestion, for example. The fragments 205 are ligated with adaptors in step 207, the adaptor ligated fragments 209 are fragmented in step 211 using a method that is sensitive to methylation, for example HpaII digestion. If the HpaII site is methylated (indicated by an *) the site is resistant to cleavage by HpaII and fragment 209 remains intact. If the HpaII site is unmethylated it is cleaved to form fragments 213 and 213 which have adaptors on only one end. In a subsequent amplification step 217 only the intact adaptor ligated fragments are amplified to form amplicons 219 and the sample is amplified by PCR using primers to the adaptor sequences, see FIG. 2. See also, Huang et al., *Hum. Mol. Genet.* 8:459-470 (1999), Yan et al., Clin. Cancer Res. 6:1432-8 (2000) and U.S. Pat. No. 6,605,432. For an explanation CpG islands and methods of analysis of methylation using microarray methods see, *Promoter and CpG Island Microarrays*, Winegarden and Takashi (eds.) DNA Press (2005).

In some embodiments the methods include treatment of the sample with bisulfite. Unmethylated cytosine is converted to uracil through a three-step process during sodium bisulfite modification. The steps are sulphonation to convert cytosine to cytosine sulphonate, deamination to convert cytosine sulphonate to uracil sulphonate and alkali desulphonation to convert uracil sulphonate to uracil. Conversion on methylated cytosine is much slower and is not observed at significant levels in a 4-16 hour reaction. See Clark et al., *Nucleic Acids Res.*, 22(15):2990-7 (1994). If the cytosine is methylated it will remain a cytosine. If the cytosine is unmethylated it will be converted to uracil. When the modified strand is copied, through, for example, extension of a locus specific primer, a random or degenerate primer or a primer to an adaptor, a G will be incorporated in the interrogation position (opposite the C being interrogated) if the C was methylated and an A will be incorporated in the interrogation position if the C was unmethylated. When the double stranded extension product is amplified those Cs that were converted to U's and resulted in incorporation of A in the extended primer will be replaced by Ts during amplification. Those Cs that were not modified and resulted in the incorporation of G will remain as C.

Kits for DNA bisulfite modification are commercially available from, for example, Human Genetic Signatures' Methyleasy and Chemicon's CpGenome Modification Kit. See also, WO04096825A1, which describes bisulfite modification methods and Olek et al. *Nuc. Acids Res.* 24:5064-6 (1994), which discloses methods of performing bisulfite treatment and subsequent amplification on material embedded in agarose beads.

Bisulfite treatment allows the methylation status of cytosines to be detected by a variety of methods. For example, any method that may be used to detect a SNP may be used, for examples, see Syvanen, *Nature Rev. Gen.* 2:930-942 (2001). Methods such as single base extension (SBE) may be used or hybridization of sequence specific probes similar to allele specific hybridization methods. In another aspect the Molecular Inversion Probe (MIP) assay may be used.

The following Examples are offered by way of illustration only, and not by way of limitation.

EXAMPLE 1

Human CpG island array. Sequences used in the design of the Human CpG Island Array were selected from NCBI human genome assembly (Build 35, UCSC hg17, May 2004). Repetitive elements were removed by RepeatMasker. There are total of 27,801 CpG islands annotated by UCSC in NCBI human genome assembly, as defined by an algorithm that measures expected versus observed CpG composition, given the GC content of the segment. CpG islands were also filtered for GC content 50% or greater and length greater than 200 bp. For a majority of the CpG islands, 8 probes were selected as a probe set to represent each island. For the islands larger than 5 kb, three probe sets (8 probes each) were selected.

The 27,801 islands represent an initial set of 27,771 that was identified in a first analysis. This first analysis missed 30 islands on random chr2 and random chr10. These 30 were subsequently processed and added to the total to obtain 27,801. Of the initial 27,771 the size distribution was as follows: 5394 less than 300 bp, about 16,000 between 300 and 1,000 bp, 5064 between 100 and 2000 bp, 1237 greater than 2 kb and 177 greater than 5 kb. For the 177 islands that were greater than 5 kb probe sets were designed and included on the array for each of the 3', middle and 5' probe selection regions (PSRs) (3 distinct 8 probe sets for each island).

For the 27,771 islands there were 28,125 PSRs (27771+ 177+177). 988 PSRs failed round 1 and the failed PSRs were extended at either end by 150 bp and probe sets were re-selected in round 2. 261 PSRs failed round 2 and were extended by a further 150 bp at either end and probe sets were re-selected in a round 3. 155 PSRs failed round 3. Of these 49 had probe set scores below a cutoff threshold and 106 had no probes selected at all. Of the 106 failed islands 62 were from 5 satellite repeat regions on chromosomes 4, 7(2) and 19(2). These satellites are not likely to play a role in gene expression. The 30 islands from random chr2 and random chr10 all passed probe selection in the first round.

The 27,771 islands were analyzed by in silico restriction fragment prediction. Exemplary results are shown in Table 2. Column 1 is sequence id, column 2 is sequence length, column 3 is CpG island length, column 4 is first position of cut site i, column 5 is sequence of cut site i, column 6 is first position of cut site i+1, column 7 is sequence of cut site i+1, column 8 is length of restriction fragment generated, column 9 is number of CpG's with the fragment, column 10 indicates where the i and i+1 cut sites are relative to the cpg island: where "l" indicates left of the CpG island, "i" indicates internal (within the island) and "r" indicates right of the CpG island (the first letter denotes site i and the second letter denotes site i+1), column 11 denotes the probe set name and column 12 is the number of probes found entirely within the fragment (for the 27771 islands).

TABLE 2

| 1 | 2 | 3 | 4 | 5 | 6 | 7 | 8 | 9 | 10 | 11 | 12 |
|---|---|---|---|---|---|---|---|---|---|---|---|
| chr10_0 | 2774 | 774 | 717 | aatt | 1954 | aatt | 1258 | 78 | lr | CpG.1.1.S1 | 8 |
| chr10_1 | 2552 | 552 | 835 | aatt | 1604 | aatt | 790 | 69 | lr | CpG.2.1.S1 | 8 |
| chr10_10 | 2284 | 284 | 959 | aatt | 1533 | aatt | 595 | 35 | lr | CpG.3.1.S1 | 8 |
| chr10_100 | 2237 | 237 | 790 | aatt | 1395 | aatt | 626 | 23 | lr | CpG.4.1.S1 | 8 |
| chr10_1000 | 3149 | 1149 | 593 | aatt | 1938 | aatt | 1366 | 137 | li | CpG.5.1.S1 | 6 |
| chr10_1000 | 3149 | 1149 | 1959 | aatt | 2722 | aatt | 784 | 29 | ir | CpG.5.1.S1 | 2 |
| chr10_1001 | 2249 | 249 | 247 | aatt | 1395 | aatt | 1169 | 52 | lr | CpG.6.1.S1 | 8 |
| chr10_1002 | 2414 | 414 | 104 | aatt | 1931 | aatt | 1848 | 84 | lr | CpG.7.1.S1 | 8 |
| chr10_1003 | 2461 | 461 | 839 | aatt | 2014 | aatt | 1196 | 62 | lr | CpG.8.1.S1 | 8 |
| chr10_1004 | 2351 | 351 | 663 | aatt | 1409 | aatt | 767 | 44 | lr | CpG.9.1.S1 | 8 |
| chr10_1005 | 2313 | 313 | 728 | aatt | 1344 | aatt | 637 | 50 | lr | CpG.10.1.S1 | 7 |
| chr10_1005 | 2313 | 313 | 1383 | aatt | 1441 | aatt | 79 | 0 | rr | CpG.10.1.S1 | 1 |
| chr10_1007 | 4587 | 2587 | 965 | aatt | 4382 | aatt | 3438 | 302 | lr | CpG.12.1.S1 | 8 |
| chr10_1008 | 2300 | 300 | 485 | aatt | 2069 | aatt | 1605 | 73 | lr | CpG.13.1.S1 | 8 |
| chr10_101 | 2231 | 231 | 944 | aatt | 1522 | aatt | 599 | 33 | lr | CpG.15.1.S1 | 8 |
| chr10_1012 | 2221 | 221 | 1136 | aatt | 1452 | aatt | 337 | 18 | ir | CpG.18.1.S1 | 4 |
| chr10_1015 | 2928 | 928 | 825 | aatt | 1059 | aatt | 255 | 10 | li | CpG.21.1.S1 | 1 |
| chr10_1015 | 2928 | 928 | 1080 | aatt | 2135 | aatt | 1076 | 102 | ir | CpG.21.1.S1 | 7 |
| chr10_1017 | 3688 | 1688 | 1191 | aatt | 2764 | aatt | 1594 | 229 | ir | CpG.23.1.S1 | 8 |

EXAMPLE 2

Human Promoter 1.0R array. Sequences used in the design of the Human Promoter 1.0R Array were selected from NCBI human genome assembly (Build 34). Repetitive elements were removed by RepeatMasker. Promoter regions were selected using sequence information from 35,685 ENSEMBL genes (version 21_34d May 14, 2004), 25,172 Refseq mRNAs (NCBI GENBANK Feb. 7, 2004), and 47,062 complete-CDS mRNA (NCBI GENBANK Dec. 15, 2003). The probes selected for the Human Promoter 1.0R Array are a subset of the probes used in the Human Tiling 2.0R Array Set (P/N 900772).

Oligonucleotide probes are synthesized in situ complementary to each corresponding sequence. Probes are tiled at an average resolution of 35 bp, as measured from the central position of adjacent 25-mer probes, leaving a gap of approximately 10 bp between probes. Each promoter region covers approximately 7.5 kb upstream through 2.45 kb downstream of 5' transcription start sites. For over 1,300 cancer-associated genes, coverage of promoter regions was expanded to include additional genomic content; for these selected genes total coverage spans from 10 kb upstream through 2.45 kb downstream of transcriptional start sites. The array interrogates regions proximal to transcription start sites and contains probes for approximately 59% of CpG islands annotated by UCSC in NCBI human genome assembly (Build 34).

EXAMPLE 3

To test the method of enrichment of methylated fragments in a sample and detection of enrichment on an array a set of *Arabidopsis* genomic controls was used in combination with a CpG island array that contains probes to the *Arabidopsis* controls. The general scheme is as shown in FIG. 2. Briefly, control DNAs that are either methylated or unmethylated were fragmented with HindIII and ligated to a HindIII adaptor sequence. The adaptor ligated fragments were then digested with HpaII which is a methylation sensitive restriction enzyme. Unmethylated fragments are fragmented while methylated fragments are not. Fragmentation of the unmethylated fragments blocks PCR amplification using a primer to the adaptor so only the fragments that were methylated at the HpaII site and were not digested by HpaII will be amplified by PCR.

Figure 3B:
FIG. 3B is an image of a gel showing the results of in vitro HpaII methylation of *Arabidopsis* genomic clones followed by digestion with HpaII restriction enzyme.
Figure 3A:
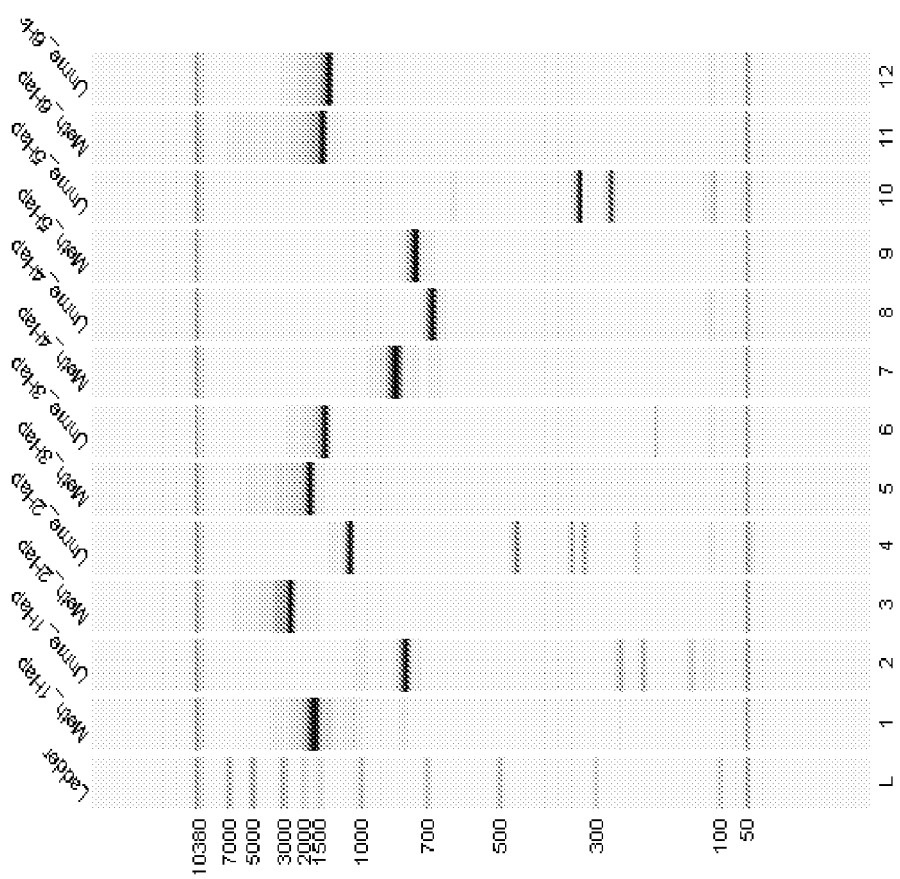
FIG. 3A is an image of a gel showing the results of in vitro HpaII methylation of *Arabidopsis* genomic clones followed by digestion with HpaII restriction enzyme.

Seven different control DNAs, Ara1, Ara2, Ara6, Ara7, Ara8, Ara9, and Ara10 were used. The controls are each a different clone of an *Arabidopsis* genomic DNA region cloned into plasmid pFC47 (Affymetrix). Inserts were confirmed by resequencing. The clones were either methylated by treatment with HpaII methylase (New England Biolabs) or are unmethylated. FIG. 3 shows confirmation of methylation by digestion of the methylated (odd numbered lanes) and unmethylated (even numbered lanes) controls with HpaII. As expected the methylated fragments (lanes 1, 3, 5, 7, 9, and 11 in 3A and 1, 3, 5 and 7 in 3B) are resistant to fragmentation by HpaII and the unmethylated fragments (lanes 2, 4, 6, 8, 10 and 12 in 3A and 2, 4, 6 and 8 in 3B) are not.

Figure 4:
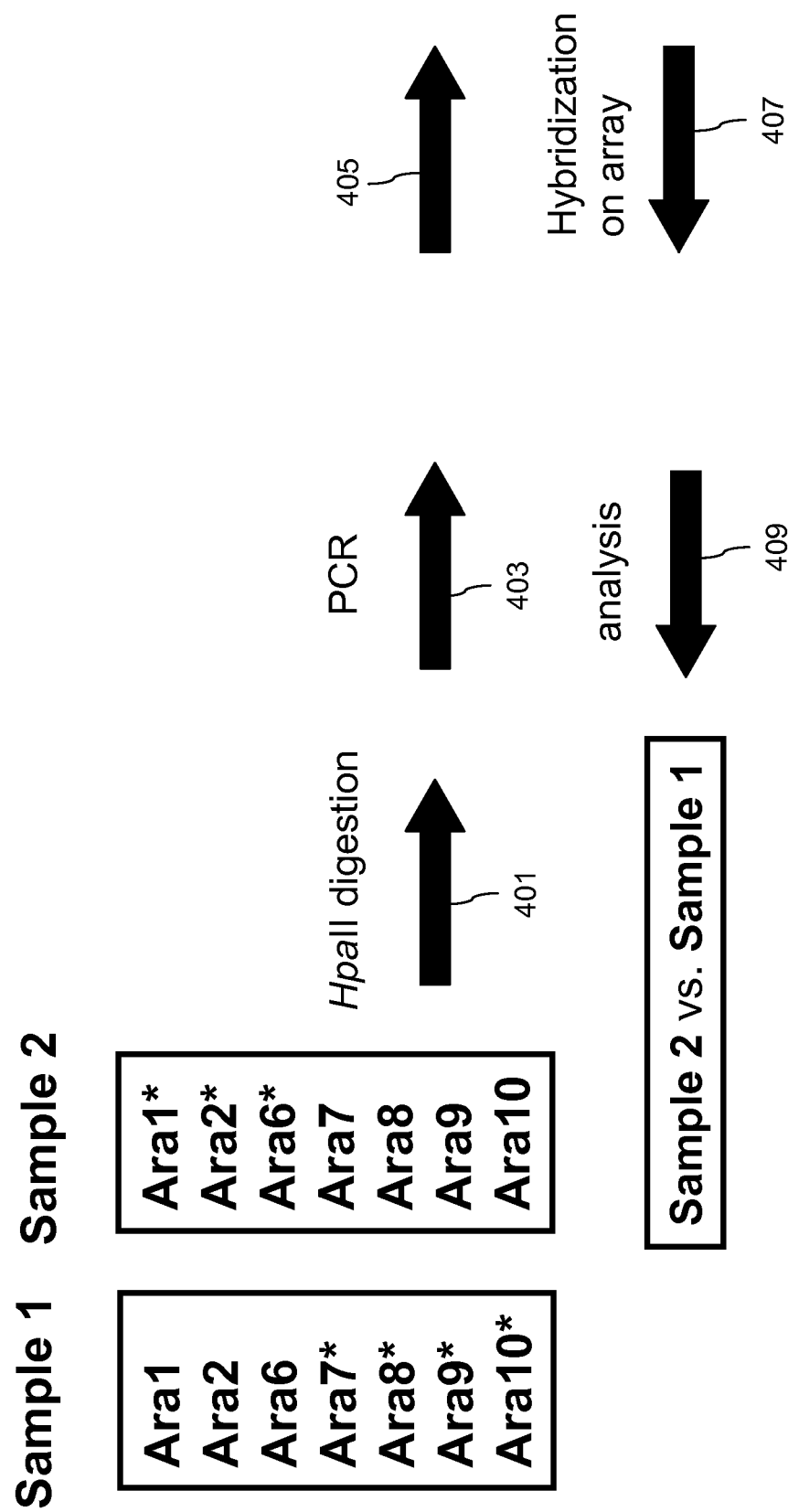
FIG. 4 is a schematic of an experiment to detect methylated DNA enriched according to the method illustrated in FIG. 2 using hybridization to an array.

Enrichment of methylated fragments in spiked samples. FIG. 4 shows the experimental design. Samples 1 and 2 are mixtures of the 7 control DNAs discussed above. In Sample 1 DNAs Ara 1, 2 and 6 are unmethylated and Ara7, 8, 9 and 10 are methylated using HpaII methylase. In Sample 2 DNAs Ara1, 2 and 6 are methylated using HpaII methylase and Ara7, 8, 9 and 10 are unmethylated. The fragments are digested with HpaII restriction enzyme in step 401 and subjected to PCR amplification in step 403 using common flanking priming sites present in pFC47, and common primers "458" and "428". The PCR amplicons were mixed with a complex background and the mixture was fragmented and labeled in step 405, hybridized to an array in step 407 and analyzed in step 409. The results for sample 2 were then compared to the results from sample 1.

Figure 5:
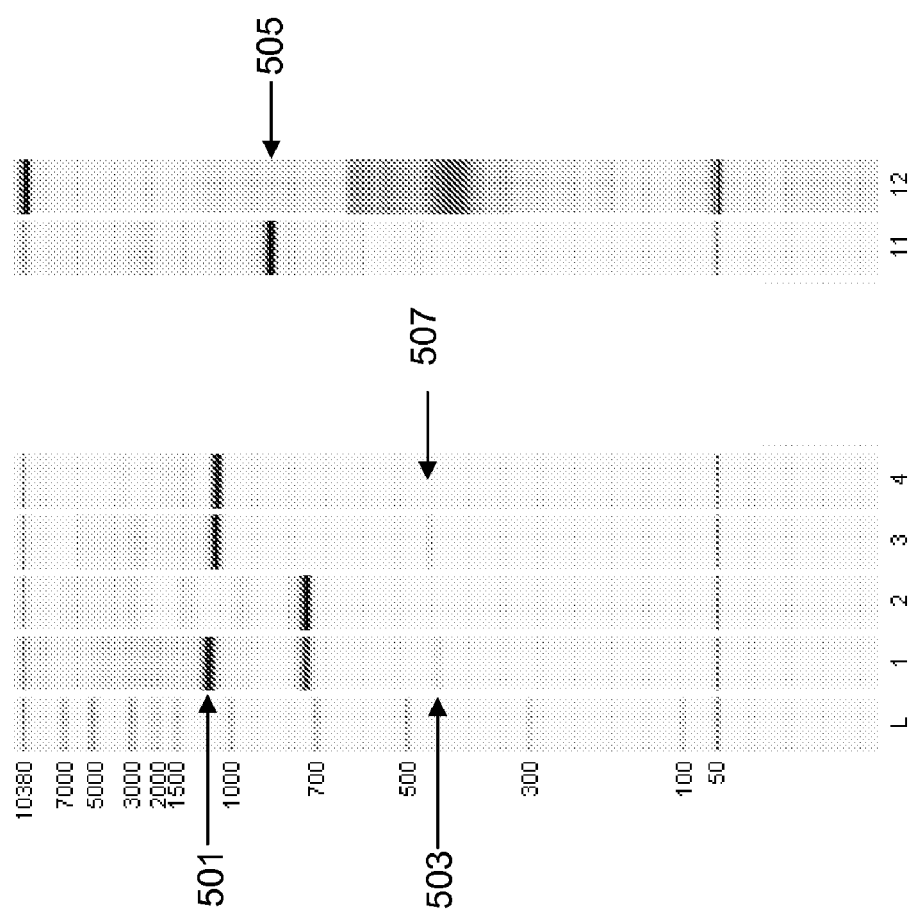
FIG. 5 is an image of a gel showing PCR amplicons of methylated and unmethylated control fragments amplified following digestion with HpaII.

An aliquot of the PCR amplicons for Ara2, 3 and 9 were separated on a gel shown in FIG. 5. Lane L is a ladder, lanes 1 and 2 are methylated and unmethylated Ara2, respectively, lanes 3 and 4 are methylated and unmethylated Ara3 and lanes 11 and 12 are methylated and unmethylated Ara9. The position of the HpaII containing fragment amplicon (501, 503, 505 and 507) are marked by arrows. The gel shows that after HpaII digestion the fragments are observed only in the methylated samples, lanes 1, 3 and 11 and not in the unmethylated samples, lanes 2, 4 and 12.

The PCR amplicons were mixed with 18 micrograms of human genomic DNA, fragmented and end labeled using DLR and TdT. Triplicate samples were generated. Approximately 1 pM of each methylated or unmethylated Ara genomic clone was used in a final 80 µl hybridization solution. The labeled, fragmented samples were hybridized to the CpG island array and the hybridization pattern was analyzed to compare Sample 1 to Sample 2. The arrays were hybridized in 1×MES, 0.7 M NaCl, 20 mM EDTA, 0.01% Tween 20, 2.5× Denhart's solution, 20 µg Cot DNA, 10% DMSO, and 40 pM oligo B2 at 45° C. for 16 hours. The arrays were washed with Affymetrix fluidics station using protocol FS450-0003 and scanned using the Affymetrix GCS3000. Cel files were generated using GCOS. Tiling Analysis Software (TAS) was used to obtain the signal intensities and p-value of pair wise comparison. Integrated Genome Browser (IGB) was applied to display and view differential signal intensities of the probes with genome location annotation.

As expected enrichment of HpaII containing fragments of Ara7, 8, 9 and 10 was observed in Sample 1 relative to Sample 2 and enrichment of HpaII containing fragments of Ara1, 2 and 6 was observed in Sample 2 relative to Sample 1. Methylated fragments were enriched relative to unmethylated fragments.

EXAMPLE 4

Mouse CpG island array. For the mouse array the data source was UCSC mm6 (March 2005). Initially 16,100 islands were identified, 5 of which were greater than or equal to 5 kb, for each of these 5 islands 3 probe sets (3', middle, and 5' PSRs) were designed and included on the array. For the other 16,095 islands a single probe set was included on the array. The total number of island PSRs used for probe selection in the first rounds was 16,110 (16,100+5+5).

During probe selection, the information was hard pruned versus the repeat database 'Repbase', and soft-pruned versus the islands themselves +/−500 bp of genomic sequence to eliminate cross-hybridization to repeats, and to reduce cross-hybridization between islands so that the signal detected is specific to a given island.

414 PSRs failed round 1, and were extended by 150 bp at either end, and subjected to a reselection of probe sets in a round 2 of probe selection. 98 PSRs failed round 2, and were subsequently extended by a further 150 bp at each end and subject to a $3^{rd}$ round of probe selection. 56 PSRs failed round 3. Of these, 26 had probe set scores below a threshold cutoff, and 30 had no probes picked at all. The 26 were included in the final array design, but the 30 were not. The array design resulted in 223,689 probes.

EXAMPLE 5

Rat CpG island array. Probe selection started using 15832 islands, of which 10 were greater than or equal to 5 kb. The 10 large islands were each divided into 3 regions for probe selection designated 3', Middle and 5' PSRs. In all there were 15,852 PSRs in the first round (15832+10+10).

During probe selection, the sequences were hard pruned versus the repeat database 'Repbase', and soft-pruned versus the islands themselves +/−500 bp of genomic sequence. The intent was to eliminate cross-hybridization to repeats, and to reduce cross-hybridization between islands, such that the signal detected would be specific to a given island, as discussed above.

535 PSRs failed round 1, and were extended by 150 bp at either end, and probe sets were re-selected in a round 2. 269 PSRs failed round 2, and were extended by a further 150 bp at either end, and probe sets were re-selected in a round 3. 189 PSRs failed round 3. Of these, 55 had probe set scores below a threshold cutoff, and 134 had no probes picked at all. The 55 were included in the final array design, but the 134 were not. The rat array design resulted in 218,637 probes.

CONCLUSION

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention may be practiced by other than the described embodiments, which are presented for purposes of illustration only and not by way of limitation. The present invention is limited only by the claims that follow.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07901882B2). An electronic copy of the "Sequence Listing" will also be available from the USPTO upon request and payment of the fee set forth in 37 CFR 1.19(b)(3).

What is claimed is:

1. An array consisting of a plurality of experimental probes each consisting of a different sequence from SEQ ID NO. 1-222,822.

2. The array of claim 1 further consisting of each of the sequences in SEQ ID NO. 1-222,822, wherein each sequence is present in a different feature of the array.

3. An array of probes consisting of:
    more than 250,000 different experimental probe features, wherein
    (a) each experimental probe feature comprises a plurality of copies of a nucleic acid probe that is different in sequence from the probes of every other feature of the array;
    (b) each probe feature is at a known or determinable location in the array; and
    (c) at least 90% of the probe features contain full length probes that are perfectly complementary to a CpG island, wherein a CpG island is a genomic region that is at least 200 bases and has a GC content of at least 50% over its length.

4. The array of claim 3 wherein the full length probes are between 20 and 100 bases in length and are complementary to human, mouse and rat genomic sequences.

5. The array of claim 3 further comprising a plurality of control features.

6. The array of claim 5 wherein the control features comprise one or more types of control features selected from the group of control feature types comprising:
    GC content matched anti-genomic controls, bacterial genome controls, *Arabidopsis* genome controls, *Pseudomonas* genome controls;
    18S rRNA gene controls, 28S rRNA gene controls; and
    probes to one or more genes that are known to be regulated by methylation.

7. The array of claim 3 wherein each probe is between 20 and 100 bases, wherein the array comprises at least 300,000 probes and wherein at least 80% of the probes comprise at least one CG dinucleotide.

8. The array of claim 7 wherein at least 50% of the probes comprise at least two CG dinucleotides.

9. The array of claim 7 wherein at least 20% of the probes comprise at least three CG dinucleotides.

* * * * *